United States Patent
Hubacz et al.

(10) Patent No.: US 11,326,980 B2
(45) Date of Patent: May 10, 2022

(54) METHOD FOR DETERMINING A PARAMETER OF AN OPTICAL DEVICE COMPRISING AT LEAST AN OPTICAL LENS

(71) Applicant: ESSILOR INTERNATIONAL, Charenton-le-Pont (FR)

(72) Inventors: Dominick Hubacz, Charenton-le-pont (FR); Stéphane Gueu, Charenton-le-pont (FR)

(73) Assignee: Essilor International, Charenton-le-Pont (FR)

( * ) Notice: Subject to any disclaimer, the term of this patent is extended or adjusted under 35 U.S.C. 154(b) by 845 days.

(21) Appl. No.: 16/071,844

(22) PCT Filed: Feb. 22, 2016

(86) PCT No.: PCT/IB2016/000320
§ 371 (c)(1),
(2) Date: Jul. 20, 2018

(87) PCT Pub. No.: WO2017/144933
PCT Pub. Date: Aug. 31, 2017

(65) Prior Publication Data
US 2021/0208024 A1 Jul. 8, 2021

(51) Int. Cl.
*G01M 11/02* (2006.01)
*G02C 7/02* (2006.01)

(52) U.S. Cl.
CPC ......... *G01M 11/0264* (2013.01); *G02C 7/022* (2013.01)

(58) Field of Classification Search
CPC ......... G01M 11/0264; G01M 11/0228; G01M 11/0207; G02C 7/022; A61B 3/0008;
(Continued)

(56) References Cited

U.S. PATENT DOCUMENTS 4,826,315 A * 5/1989 Kohayakawa ..... G01M 11/0228
356/125
5,198,867 A * 3/1993 Campbell ............ G01B 11/255
356/125
(Continued)

FOREIGN PATENT DOCUMENTS

CN 104605810 A 5/2015
EP 1 679 499 A2 7/2006
(Continued)

OTHER PUBLICATIONS

International Search Report, dated Nov. 28, 2016, from corresponding PCT application No. PCT/IB2016/000320.
(Continued)

*Primary Examiner* — Isiaka O Akanbi
(74) *Attorney, Agent, or Firm* — Nixon & Vanderhye (57) ABSTRACT

Disclosed is a method for determining a parameter of an optical device including at least an optical lens, the method including: an optical system providing step, during which an optical system including a visual target, the optical device and an image acquisition module is provided in an initial configuration state, a parameter determining step during which a parameter of the optical device is determined based on the blur level of the images of the visual target acquired by the image acquisition module through the optical device in at least two different configuration states.

19 Claims, 5 Drawing Sheets

(58) Field of Classification Search
CPC ....... A61B 3/0025; A61B 3/09; A61B 3/1035; A61B 3/14; A61B 5/6898
USPC .......................................... 356/124–127, 153
See application file for complete search history.

(56) References Cited

U.S. PATENT DOCUMENTS

| | | | | |
|---|---|---|---|---|
| 5,247,341 | A * | 9/1993 | Kurachi | G01M 11/0235 356/125 |
| 5,453,606 | A * | 9/1995 | Hojo | G01B 11/272 250/201.1 |
| 5,574,555 | A * | 11/1996 | Yamaguchi | G01M 11/0228 250/201.2 |
| 5,742,381 | A * | 4/1998 | Ueno | G01B 11/255 356/124 |
| 5,999,251 | A * | 12/1999 | Teramoto | G01M 11/0221 250/201.1 |
| 7,486,389 | B2 | 2/2009 | Imaizumi | |
| 7,760,365 | B2 * | 7/2010 | Ueki | G01M 11/0221 356/515 |
| 9,076,192 | B2 | 7/2015 | Bertheau et al. | |
| 9,971,137 | B2 * | 5/2018 | Onda | H04N 7/18 |
| 2001/0055111 | A1 * | 12/2001 | Yoda | G01M 11/0207 356/127 |
| 2006/0152709 | A1 * | 7/2006 | Imaizumi | G01M 11/0228 356/124 |
| 2009/0021725 | A1 * | 1/2009 | Kajino | G01M 11/0264 356/124 |
| 2013/0132044 | A1 | 5/2013 | Paris et al. | |
| 2015/0109613 | A1 | 4/2015 | Bull et al. | |
| 2016/0066780 | A1 | 3/2016 | Pamplona et al. | |
| 2016/0374548 | A1 * | 12/2016 | Onda | G02B 27/0068 351/206 |
| 2016/0377884 | A1 * | 12/2016 | Lau | G02C 7/022 351/159.05 |
| 2017/0027437 | A1 * | 2/2017 | Neal | A61B 3/107 |
| 2018/0064338 | A1 * | 3/2018 | Neal | A61B 3/158 |
| 2018/0064576 | A1 * | 3/2018 | Chen | A61B 3/0025 |
| 2019/0049335 | A1 * | 2/2019 | Goldberg | G01M 11/0264 |

FOREIGN PATENT DOCUMENTS

| | | |
|---|---|---|
| EP | 2 863 201 A1 | 4/2015 |
| JP | 2009-229422 A | 10/2009 |
| WO | 2012/080643 A1 | 6/2012 |
| WO | 2014/169148 A1 | 10/2014 |

OTHER PUBLICATIONS

Office Action issued in Chinese Patent Application No. 201680001044.3 dated May 6, 2020 with English translation provided.

* cited by examiner

METHOD FOR DETERMINING A PARAMETER OF AN OPTICAL DEVICE COMPRISING AT LEAST AN OPTICAL LENS

FIELD OF THE INVENTION

The invention relates to a method for determining a parameter of an optical device comprising at least an optical lens and an optical device parameter determining module.

BACKGROUND OF THE INVENTION

Usually, a person wishing to have an optical equipment goes to see an eye care practitioner.

The eye care practitioner orders the eyewear equipment at an optical lab by sending an order request to the optical lab. The order request may comprise wearer data, for example the wearer's prescription, fitting data, spectacle frame data, for example the type of spectacle frame the wearer has selected, and lens data, for example the type of optical lens the wearer has selected.

The determination of the wearer's prescription may require carrying out complex and time consuming measurements. Such measurements usually require complex and costing material and qualified personnel to be carried out.

Such measurements are usually carried out even when the person's optical needs have not changed. For example a person that wants to order a new frame or change his/her lenses because they are damaged or order a second pair with the same prescription than that of his/her previous spectacles may have to go through the tedious process indicated previously if he/she doesn't have his/her prescription paper anymore.

The eye care practitioner may use lens mapper and/or lens meter to determine the optical features of the current optical lenses of the optical equipment of the person. However, such devices still require going to the eye care practitioner since there are very expensive and require qualified person to be used. In other words, the person himself may not use such devices to determine the parameters to be included in the order request. Typically such devices are not available when a person wishes to order a new optical equipment over the internet at home.

Therefore, there is a need for a method and a device that would allow a person to quickly, easily and at low cost determined optical parameters of an optical device.

One object of the present invention is to provide such method.

SUMMARY OF THE INVENTION

To this end, the invention proposes a method for determining a parameter of an optical device comprising at least an optical lens, the method comprising:
- an optical system providing step, during which an optical system comprising a visual target, the optical device and an image acquisition module is provided in an initial configuration state,
- a parameter determining step during which a parameter of the optical device is determined based on the blur level of the images of the visual target acquired by the image acquisition module through the optical device in at least two different configuration states.

Advantageously, the method of the invention allows a person to determine optical parameters of an optical device by simply adapting the configuration of the optical system so as to adjust the blur level of images of a visual target acquired by the image acquisition module through the optical device. The method of the invention may be implemented using a portable electronic device, such as a smartphone, a tablet computer or a laptop.

The method of the invention may be used for mass distribution programs such as eyeglass donation programs done by non-governmental organizations requiring great "mobility", for example in geographic zone that are poorly equipped in optical centers.

According to further embodiments which can be considered alone or in combination:
- the method further comprises prior to the parameter determining step:
  - an initial image acquisition step, during which an image of the visual target through the optical device is acquired by the image acquisition module with the optical system in an initial configuration state,
  - an optical system configuration modifying step, during which the configuration of the optical system is modified into a modified configuration state,
  - a modified image acquisition step, during which an image of the visual target through the optical device is acquired by the image acquisition module with the optical system in the modified configuration state; and/or
- the optical system configuration modifying step and the modified image acquisition step are repeated until the configuration of the optical system that minimizes the blur level of the images of the visual target acquired by the image acquisition module through the optical device is determined; and/or
- the parameter of the optical device to be determined is the optical power at a reference point of the optical device; and/or
- the parameter of the optical device is determined based on the configuration of the optical system that minimizes the blur level of the images of the visual target acquired by the image acquisition module through the optical device; and/or the optical device is a spherical optical lens; and/or
- the optical device is an astigmatic optical lens and the parameter of the optical lens to be determined is the cylindrical power that is determined based on the two configurations of the optical system that minimize the blur level of the images of the visual target acquired by the image acquisition module through the optical lens; and/or
- the optical device is an astigmatic optical lens and the parameter of the optical lens to be determined is the axis of the cylinder of the optical lens that is determined based on the spatial distribution of blur level over at least one image of the visual target acquired acquisition module through the optical lens; and/or
- the configuration of the optical system that minimizes the blur level of the images of the visual target acquired by the image acquisition module through the optical device is determined by an interpolation method; and/or
- the method further comprises prior to the acquisition of an image by the image acquisition module of the visual target through the optical device a control step during which at least one of the relative position and orientation of the different elements of the optical system is determined; and/or
- the visual target comprises spatial frequency variable in frequency and/or in orientation; and/or during the optical system providing step the target and the optical device are placed along the optical axis of the image acquisition module; and/or the optical lens of the optical device is placed such that its optical axis is aligned with the optical axis of the image acquisition module and the mean plan of the visual target is perpendicular to the optical axis of the image acquisition module; and/or the image acquisition module is configured to focus on infinite and during the optical system configuration modifying step only the position of the optical device along the axis from the visual target to the image acquisition module is modified; an/or when the optical power of the optical lens of the optical device is negative, the method further comprises an additional optical lens providing during which an addition optical lens having a positive optical power greater in absolute value than the estimated negative optical power of the optical lens of the optical device is provided, the additional optical lens is maintained as close as possible to the optical lens of the optical device during the different steps of the method; and/or the method further comprises prior to the optical system providing step a focus setting step during which the focus of the image acquisition module is set so as to provide a sharp image of the visual target when placed at an initial distance and acquired directly by the image acquisition module, during the optical system providing step the optical device is placed as close as possible to the image acquisition module, and during the optical system configuration modifying step only the relative position of the visual target along the axis from the visual target to the image acquisition module is modified; and/or the method further comprises prior to the optical system providing step a focus setting step during which the focus of the image acquisition module is set so as to provide a sharp image of the visual target when placed at a given distance and acquired directly by the image acquisition module, during the optical system providing step the optical device is placed as close as possible to the image acquisition module, and during the an optical system configuration modifying step only the focus of the image acquisition module is modified; and/or the configuration data indicative of the configuration of the optical system can be determined manually with tools enabling to measure distances; and/or when characteristics of the target and/or the acquisition module is known, the configuration data indicative of the configuration of the optical system can be determined automatically by using the images acquired in the different configurations; and/or the acquisition module further comprises a communication module arranged to communicate configuration data indicative of the configuration of the optical system and image data indicative of a image of the visual target acquired by the image acquisition module through the optical device.

The invention also relates to an optical device parameter determining module comprising:

a communication component configured to receive configuration data indicative of different configuration states of an optical system comprising a visual target, an optical device and an image acquisition module and image data indicative of a images of the visual target acquired by the image acquisition module through the optical device in difference configuration states, a memory storing computer executable instructions and configured to store the received data; and a processor for executing the computer executable instructions, wherein the computer executable instructions comprises instructions for determining a parameter of the optical device based on the blur level of the images of the visual target acquired by the image acquisition module through the optical lens in different configuration states.

The invention further relates to a computer program product comprising one or more stored sequences of instructions that are accessible to a processor and which, when executed by the processor, causes the processor to carry out at least the steps of the method according to the invention.

The invention also relates to a computer-readable storage medium having a program recorded thereon; where the program makes the computer execute at least the steps of the method of the invention.

The invention further relates to a device comprising a processor adapted to store one or more sequence of instructions and to carry out at least steps of the method according to the invention.

BRIEF DESCRIPTION OF THE DRAWINGS

Embodiments of the invention will now be described, by way of example only, and with reference to the following drawings in which.

DETAILED DESCRIPTION OF PREFERRED EMBODIMENTS

Elements in the figures are illustrated for simplicity and clarity and have not necessarily been drawn to scale. For example, the dimensions of some of the elements in the figure may be exaggerated relative to other elements to help improve the understanding of the embodiments of the present invention.

Figure 1:
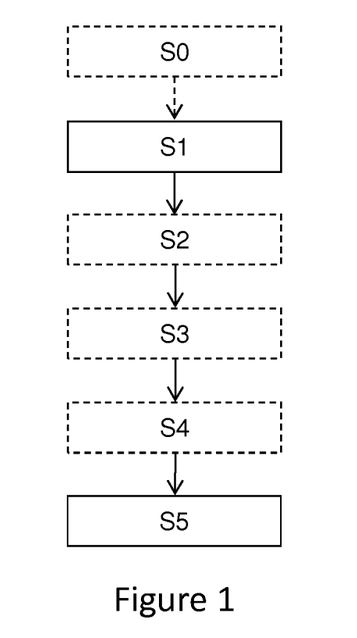
FIG. 1 is a flow chart representing a method for determining a parameter of an optical device according to the invention.

As illustrated on FIG. 1, the method for determining a parameter of an optical device comprising at least an optical lens, according to the invention comprises at least:

an optical system providing step S1, and
a parameter determining step S5.

Figure 2:
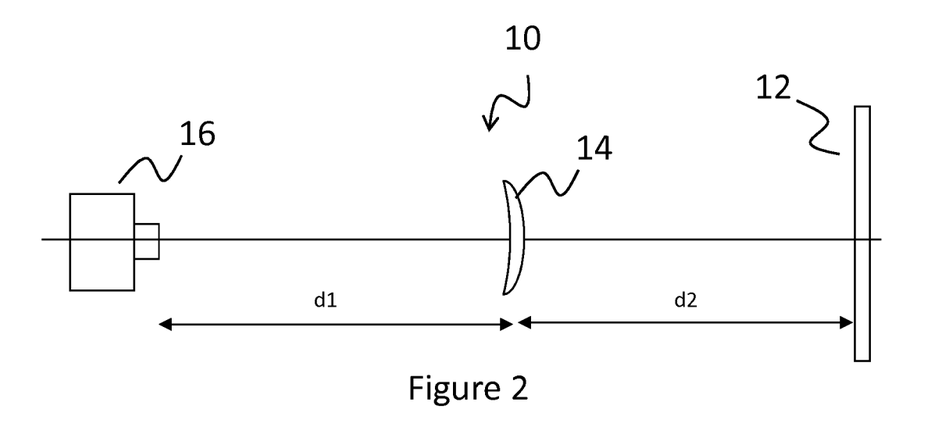
FIG. 2 is a schematic representation of an optical system that may be provided during the method of the invention.

During the optical system providing step S1, an optical system as illustrated on FIG. 2 is provided. The optical system 10 comprises a visual target 12, an optical device 14 and an image acquisition module 16. During the optical system providing step S1 the optical system 10 is provided in an initial configuration state.

The visual target may be a real word scene such as buildings or trees in the landscape. Furthermore, the visual target 12 may be a more control visual target for example a pattern whose geometric shape and spatial frequency are adapted for the method of the invention. It may be displayed on a printed chart, or on a computer or tablet display.

Preferably, the visual target comprises spatial frequency variable in frequency and/or in orientation, for example the visual target comprises radial fringes as illustrated on FIG. 3. Preferably, visual target have high contrast level so as to facilitate the determination of blur.

The optical device 14 comprises at least an optical lens. In the following description, the invention is described with the optical device being an optical lens. However, it is clear for the person skilled in the art that the method of the invention may be used for a more complex optical device, for example comprising an assembly of optical lenses such as to form for example a camera lens. It may apply in particular to eyewear having two prescription lenses mounted in it, and being the current eyewear of the user of this invention.

According to a preferred embodiment, the parameter of the optical device 14 to be determined is the optical power at a reference point of the optical device. For example, the parameter may be the optical power at optical center of the optical device, at the fitting cross, the prism reference points or any other reference point that may be identified either directly or indirectly on the optical lens.

For example, when the optical lens is a spherical optical lens, the spherical optical power of the lens may be determined by the method of the invention. When the optical lens is an astigmatic optical lens the cylindrical power and/or the axis may be determined using the method of the invention.

The image acquisition module 16 is for example a camera, for example a CMOS camera or a CCD camera.

According to an embodiment, the image acquisition module 16 is a camera of a portable electronic device such as a smart phone, a personal digital assistant, a tablet computer, smart frame or smart watch.

The portable electronic device preferably comprises a memory to store executable computer programs and data and a processor to execute the stored computer program. The portable electronic device may further comprise a communication unit to allow the portable electronic device to communicate data with distant device. The communication unit may be configured either for a wire connection or a wireless connection using for example WIFI or Bluetooth® technology.

The wire connection may also by a USB type. The portable electronic device may comprise a memory storing data and the data may be communicated to distant entity using a cable connection.

According to an embodiment of the invention, during the optical system providing step, the visual target 12 and the optical device 14 are placed along the optical axis of the image acquisition module 16.

Preferably the optical lens of the optical device is placed such that its optical axis is aligned with the optical axis of the image acquisition module and the mean plan of the visual target is perpendicular to the optical axis of the image acquisition module.

During the parameter determining step S5, a parameter of the optical device 14 is determined based on the blur level of the images of the visual target acquired by the image acquisition module through the optical device in at least two different configuration states.

For example, the parameter of the optical device may be determined based on the configuration of the optical system that minimizes the blur level of the images of the visual target acquired by the image acquisition module through the optical device.

The determination of the blur level may use several known technics such as the ones described in the Chapter 10.3 "Analyse de la netteté d'une image numérique" of the book "Analyse et traitement des signaux—2ème edition— Méthodes et applications" by Etienne Tisserand, Jean-François Pautex and Patrick Schweitzer. Further example of blur level determination technics are described in document WO 2012080643 A1.

The evaluation of the blur level can be based on the analysis of the distribution of the image grey levels.

Figure 3A:
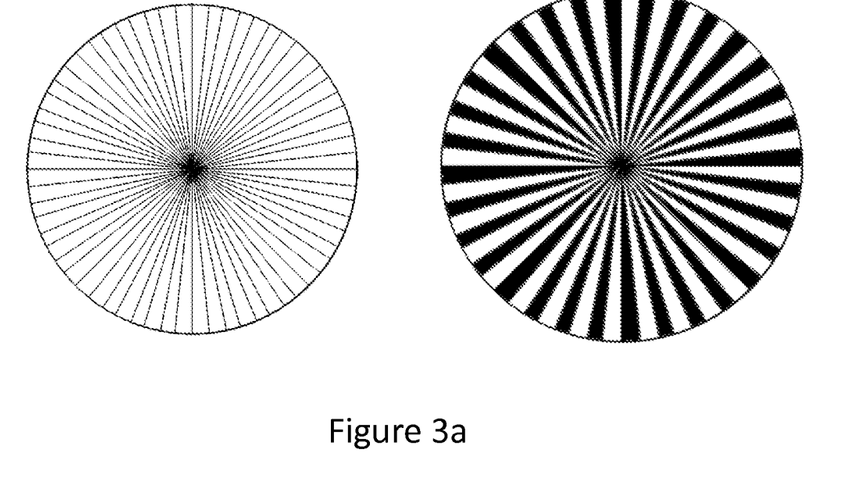
FIG. 3a represents visual targets that may be used in the method of the invention.
Figure 3B:
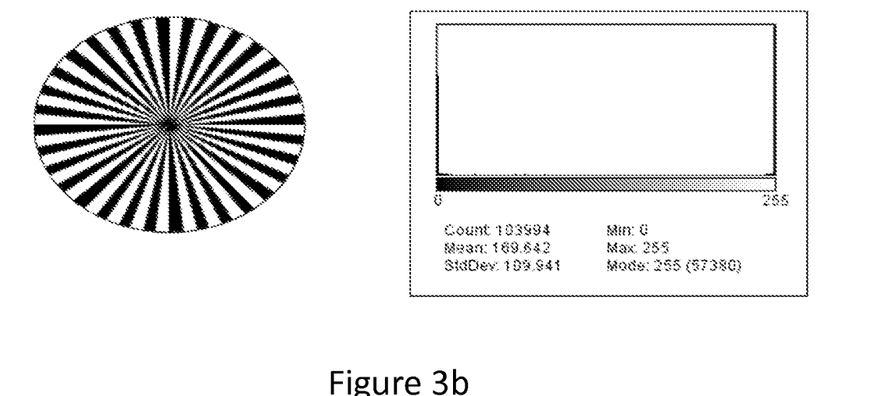
FIGS. 3b to 3f represent images of visual targets and corresponding grey level histograms of a visual target through different optical lenses.
Figure 3C:
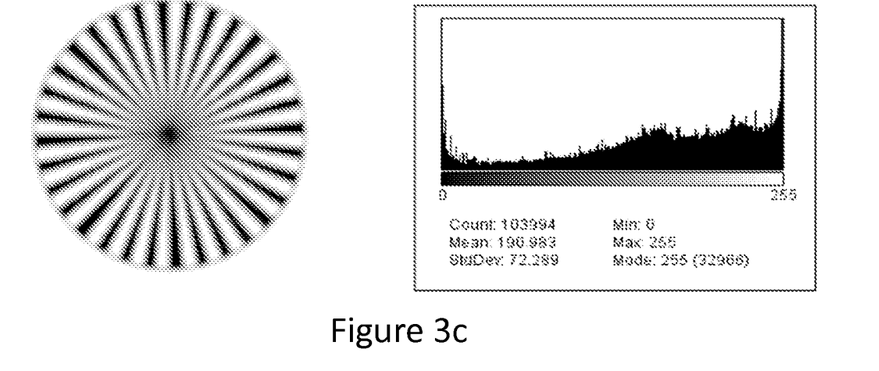

FIG. 3b represents the sharp image of a visual target through a single vision lens and the corresponding grey level histogram. FIG. 3c represents a blurred image of the visual target through the single vision lens and the corresponding grey level histogram.

Figure 3D:
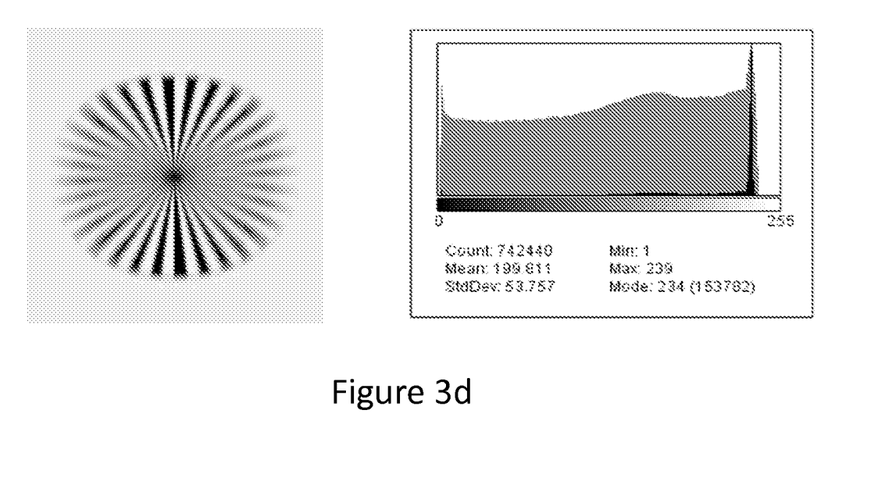

FIG. 3d represents the image of a visual target through a toric lens having a sphere of 1.5 diopters, a cylinder of 1 diopter and an axis of 90° and the corresponding grey level histogram when the toric lens is at the first focus point.

Figure 3E:
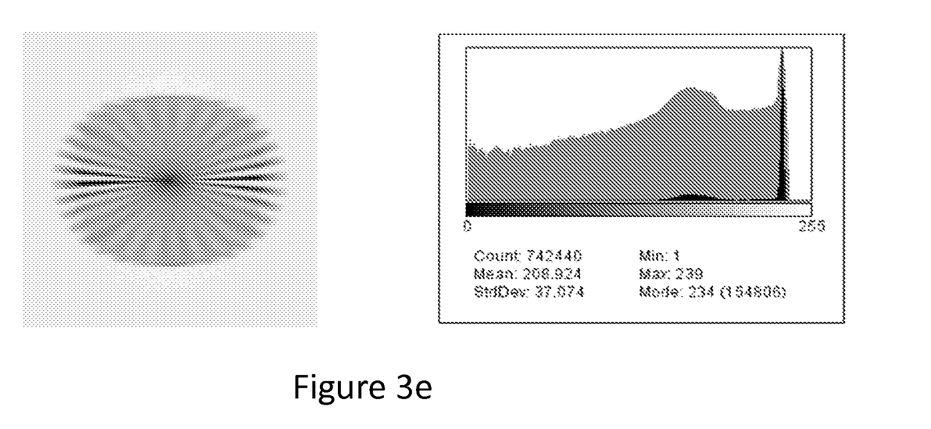

FIG. 3e represents the image of the visual target through the toric lens and the corresponding grey level histogram when the toric lens is at the second focus point.

Figure 3F:
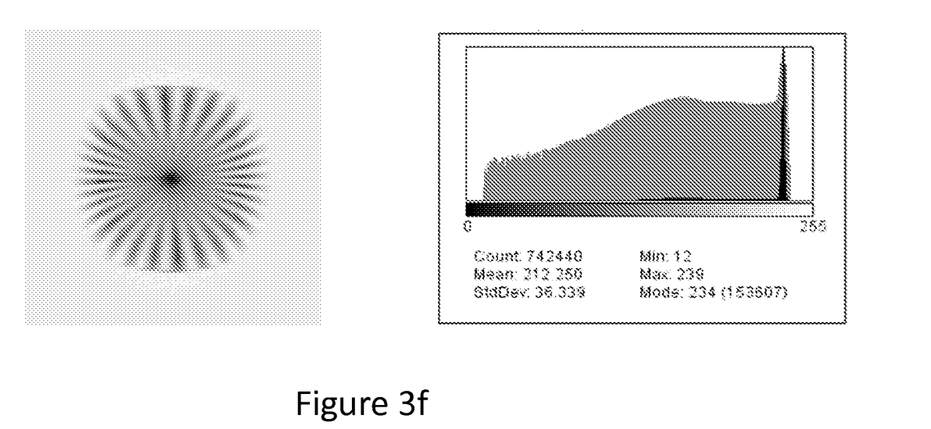

FIG. 3f represents a blurred image of the visual target through the toric lens and the corresponding grey level histogram when the toric lens is placed at a distance comprised between the first and second focus points.

According to an embodiment of the invention, the configuration of the optical system that minimizes the blur level of the images of the visual target acquired by the image acquisition module through the optical device is determined by an interpolation method.

As illustrated on FIG. 1, the method according to the invention may further comprise prior to the parameter determining step:

an initial image acquisition step S2,
an optical system configuration modifying step S3, and
a modified image acquisition step S4.

During the initial image acquisition step S2, an image of the visual target through the optical device is acquired by the image acquisition module with the optical system in an initial configuration state.

The configuration of the optical system is then modified during the optical system configuration modifying step S3 so as to have the optical system in a modified configuration state different from the initial configuration state. Typically, during optical system configuration modifying step, the at least one of the optical lens, the visual target and the image acquisition module is moved along the optical axis of the optical system.

During the modified image acquisition step S4, an image of the visual target through the optical device is acquired by the image acquisition module with the optical system in the modified configuration state.

The parameter of the optical device may be determined based on the blur level of the images acquired by the image acquisition module through the optical device in the different configuration states of the optical system.

In an embodiment of the invention, the optical system configuration modifying step and the modified image acquisition step are repeated until the configuration of the optical system that minimizes the blur level of the images of the visual target acquired by the image acquisition module through the optical device is determined.

As indicated previously, the configuration of the optical system that minimizes the blur level of the images of the visual target acquired by the image acquisition module through the optical device may be determined by an interpolation method. According to such embodiment, the optical system configuration modifying step and the modified image acquisition step may be repeated a few, for example 3 to 6 times so as to implement interpolation between the different configuration and the level of blur. The number of iterations is fixed to obtain the best compromise between the time of measurement and the final accuracy of the measurement.

When the optical device comprises or is an astigmatic/toric optical lens and the parameter of the optical lens to be determined is the cylindrical power, two configurations of the optical system are to be determined. According to such embodiment, the two configurations of the optical system that minimize the blur level of the images of the visual target acquired by the image acquisition module through the optical lens are determined. In the case of an astigmatic/toric lens, the blur will be determined not necessarily as a global blur, but may be determined for specific part of the target, that exhibits specific orientation. For instance, when using the target of FIG. 3, the blur will depend on the radial orientation in presence of astigmatism on the lens, and we can define the blur of the target as being the blur of the radial orientation that exhibits maximum sharpness.

The method of the invention may further comprise determining the axis of an astigmatic/toric optical lens. In particular the axis is determined based on the spatial distribution of blur level over at least one image of the visual target acquired acquisition module through the optical lens.

The method according to the invention may further comprise prior to the acquisition of an image by the image acquisition module of the visual target through the optical device a control step during which at least one of the relative position and orientation of the different elements of the optical system is determined.

Typically, the image acquisition module is a camera of portable electronic device and such device may move upon carrying out the different steps of the method. Therefore, it may be best to control the relative position and orientation of the different elements of the optical system.

Relative positions may be determined using optical and/or telemetric means. The relative movements of the acquisition module may be determined using accelerometer and gyroscope of the smartphone.

For example, during the images acquisition steps, it is best to be sure that centering and axing are correct for both fixed and moving elements. The control is based on the use of the position, the shape and the boundaries of the image of the visual target acquired through the optical device.

Such control may be done with an Apps' wizard consisting in acquiring live video and helping the user to find the good position which enables him/her to have a correct image of the visual target.

The same wizard may be used or the selection of the correct images can be done by the App which eliminates the bad images, for example image being blurred because of user tremor or images containing elements of the target that are not visible, and informs the user if the measurement has to be performed again due to a lack of images.

According to an embodiment of the invention, the image acquisition module may be configured to focus on infinite.

Figure 4A:
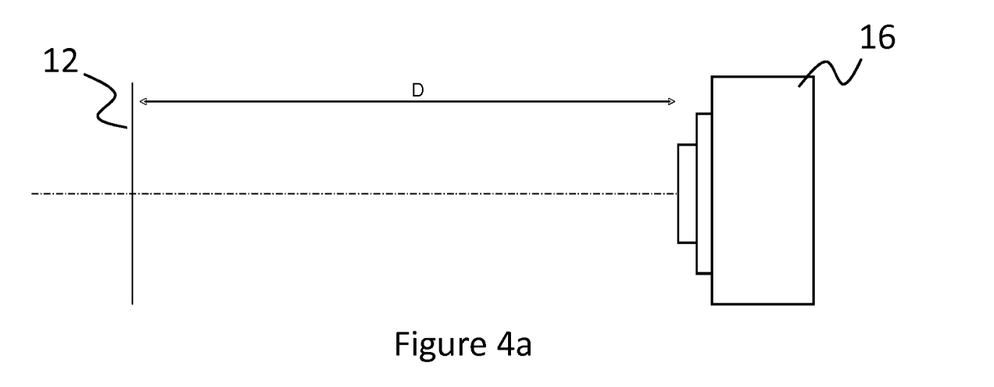
FIGS. 4a and 4b are schematic representation of an optical system in different configuration states.

As illustrated on FIG. 4a, first without any optical device, the visual target is positioned at a first distance D from the image acquisition module, with D being greater than the focal distance of the image acquisition module, for example D is about 1 m. Due to the difference between the distance D and the focal length of the image acquisition module, the image of the visual target acquired by the image acquisition module through the optical device is sharp.

Figure 4B:
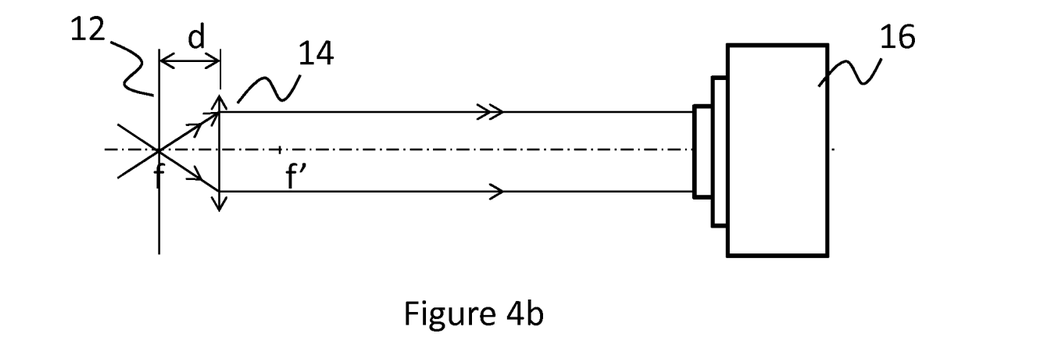

As illustrated on FIG. 4b, the optical device is placed between the visual target and the image acquisition module in an initial position providing the optical system in an initial configuration. As indicated previously, during the optical system providing step the visual target and the optical device are placed along the optical axis of the image acquisition module and such that the optical axis of the optical device is aligned with the optical axis of the image acquisition module and the mean plan of the visual target is perpendicular to the optical axis of the image acquisition module.

During the optical system configuration modifying step only the position of the optical device along the axis from the visual target to the image acquisition module is modified.

The configuration state of the optical system that minimizes the blur level of the images of the visual target acquired by the image acquisition module through the optical device is when the optical device is placed such that the visual target is at the focal plan of the optical device.

In such configuration, the distance between the visual target and the optical device provides the focal distance of the lens. The optical power may be determined as the inverse of such distance.

The measurement of the distance between the visual target and the lens can be done with a ruler and/or a telemeter integrated to the image acquisition module, and/or images of reference element of known dimension taken with the image acquisition module.

If the optical power of the optical device is negative it may be impossible to determine the optical power using the image acquisition module focused at infinity. Indeed, it will be no possible to have the target positioned at the focal point of the lens, because this point is virtual.

To overcome such issue, the method may further comprises an additional optical lens providing during which an additional optical lens having a positive optical power greater in absolute value than the estimated negative optical power of the optical lens of the optical device is provided. For example the additional optical lens may have a 25 diopter power. The additional optical lens is maintained as close as possible to the optical lens of the optical device during the different steps of the method.

The optical power of the new optical device consisting of the initial optical device of which the optical is to be determined and the additional optical lens corresponds to the addition of the optical power of the optical device and the additional optical lens whose value is known Therefore, applying the method of the invention to the new optical device allows determining the optical power of the initial optical device.

According to a further embodiment of the invention, the method further comprises prior to the optical system providing step a focus setting step S0 during which the focus of the image acquisition module is set so as to provide a sharp image of the visual target when placed at an initial distance and acquired directly by the image acquisition module. Preferably, the initial distance is smaller than 1 meter, for example around 50 cm.

The setting of the image acquisition module is fixed.

The optical device is placed between the visual target and the image acquisition module, preferably as close as possible to the image acquisition module. The image of the visual target acquired by the image acquisition module through the optical lens is then blur.

During the optical system configuration modifying step only the relative position of the visual target along the axis from the visual target to the image acquisition module is modified.

Even if the focal length of the image acquisition module is not known, it is possible to determine the focal length of the ophthalmic lens calculation taking into account the distance d2−d1 between the two positions of the visual target without and with the optical device for which the blur is minimal. For example, the distances d1 and d2 can be measured using a ruler or a telemeter device.

Another solution to measure the optical power of the optical device consists in keeping both the visual target and the image acquisition module fixed and changing the focus of the image acquisition module.

Figure 5A:
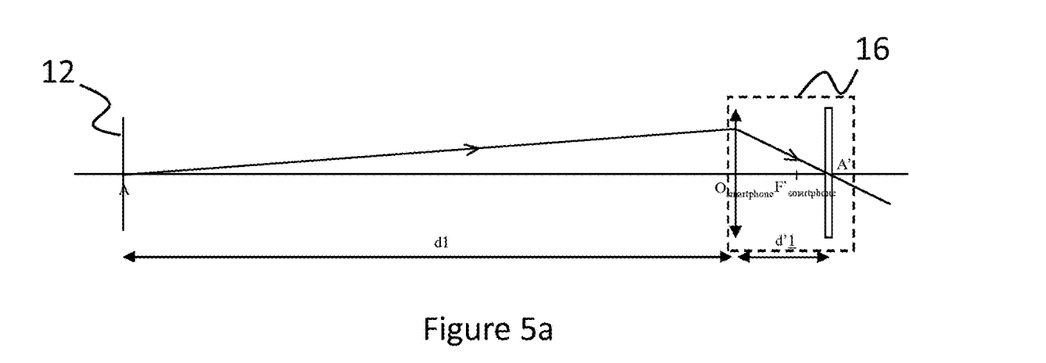
FIGS. 5a and 5b are schematic representation of an optical system in different configuration states.

As illustrated on FIG. 5a, first the image acquisition module is configured so as to acquire a sharp image of the visual target without the optical device.

During the optical system providing step the optical device is placed as close as possible to the image acquisition module. The image of the visual target acquired by the image acquisition module through the optical device is then blurry.

Figure 5B:
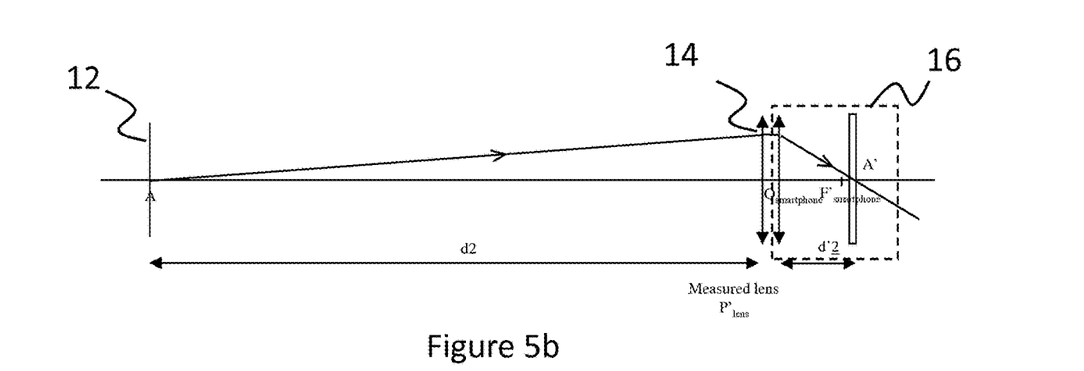

As illustrated on FIG. 5b, during the an optical system configuration modifying step only the focus of the image acquisition module is modified so as to obtain a sharp image of the visual target through the optical device.

In this case, the optical power of the optical device is $P=1/d'2+1/d2-1/d'1-1/d1$, with d1 the initial distance between the lens of the image acquisition module and visual target, d'1 the initial distance between the lens of the image acquisition module and the acquisition sensor, d2 the distance between the optical device in the configuration state that minimizes the blur and the visual target (d2~d1), and d'2 the distance between the lens of the image acquisition module and the acquisition sensor in the configuration state that minimizes the blur.

Since d1 is substantially equal to d2 and that both are much greater than d'1 and d'2 that are substantially equal to each other, the optical power of the optical device may be considered as $P=1/d'2-1/d'1$. As illustrated on FIG. 6, the invention further relates to an optical lens determining module 20 comprising a communication component 22, a memory 24 and a processor 26.

Figure 6:
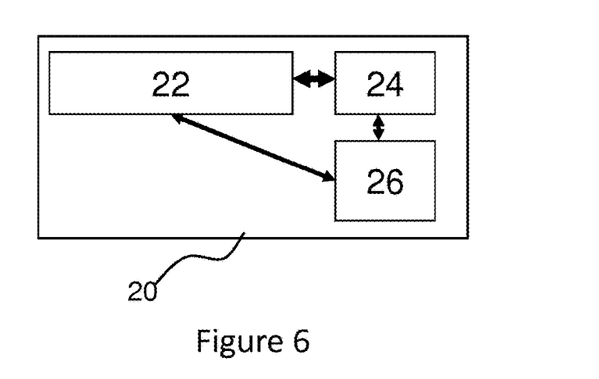
FIG. 6 is a schematic representation of an optical device parameter determining module according to the invention.

The communication component 22 may be configured to receive configuration data indicative of different configuration states of an optical system comprising a visual target, an optical device and an image acquisition module and image data indicative of images of the visual target acquired by the image acquisition module through the optical device in difference configuration states.

The memory 24 may store computer executable instructions and configured to store the received data. The computer executable instructions comprises instructions for determining a parameter of the optical device based on the blur level of the images of the visual target acquired by the image acquisition module through the optical lens in different configuration states. Typically, the computer executable instructions are configured to implement the different determining methods disclosed previously.

The processor 26 is configured to execute the computer executable instructions.

The invention has been described above with the aid of embodiments without limitation of the general inventive concept; in particular the mounted sensing device is not limited to a head mounted device.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method for determining a parameter of an optical device comprising at least an optical lens, the method comprising:

an optical system providing step, during which an optical system is provided in an initial configuration state, said optical system comprising a visual target, the optical device, and an image acquisition module, the image acquisition module comprising a camera, and the image acquisition module being pre-configured by way of a focus setting step, carried out prior to the optical system providing step, that comprises setting a focus of the image acquisition module so as to provide a sharp image of the visual target when placed at an initial distance and acquired directly by the image acquisition module;

a parameter determining step during which a parameter of the optical device is determined based on a blur level of images of the visual target acquired by the image acquisition module through the optical device in at least two different configuration states;

a focus modifying step, during which the focus of the image acquisition module is modified so as to bring the configuration of the optical system into a modified configuration state different from the initial configuration state;

a modified image acquisition step, during which an image of the visual target through the optical device is acquired by the image acquisition module with the modified focus of the optical system in the modified configuration state, wherein:

during the optical system providing step, the optical device is placed as close as possible to the image acquisition module, and during the focus modifying step, only the focus of the image acquisition module is modified.

2. The method according to claim 1, wherein the method further comprises prior to the parameter determining step:

an initial image acquisition step, during which an initial image of the visual target through the optical device is acquired by the image acquisition module with the optical system in the initial configuration state.

3. The method according to claim 2, wherein the focus modifying step and the modified image acquisition step are repeated until a configuration of the optical system that minimizes the blur level of the images of the visual target acquired by the image acquisition module through the optical device is determined.

4. The method according to claim 2, wherein the parameter of the optical device to be determined is the optical power at a reference point of the optical device.

5. The method according to claim 3, wherein the parameter of the optical device to be determined is the optical power at a reference point of the optical device.

6. The method according to claim 2, wherein the parameter of the optical device is determined based on a configuration of the optical system that minimizes the blur level of the images of the visual target acquired by the image acquisition module through the optical device.

7. The method according to claim 3, wherein the parameter of the optical device is determined based on the configuration of the optical system that minimizes the blur level of the images of the visual target acquired by the image acquisition module through the optical device.

8. The method according to claim 1, wherein the parameter of the optical device to be determined is the optical power at a reference point of the optical device.

9. The method according to claim 1, wherein the parameter of the optical device is determined based on a configuration of the optical system that minimizes the blur level of the images of the visual target acquired by the image acquisition module through the optical device.

10. The method according to claim 1, wherein the optical device is an astigmatic optical lens, and the parameter of the optical lens to be determined is a cylindrical power that is determined based on the two configurations of the optical system that minimize the blur level of the images of the visual target acquired by the image acquisition module through the optical lens.

11. The method according to claim 1, wherein a configuration of the optical system that minimizes the blur level of the images of the visual target acquired by the image acquisition module through the optical device is determined by an interpolation method.

12. The method according to claim 1, wherein the method further comprises prior to acquisition of an image by the image acquisition module of the visual target through the optical device:
a control step during which at least one of a relative position and an orientation of different elements of the optical system is determined.

13. The method according to claim 1, wherein the visual target comprises a spatial frequency variable in frequency and/or in orientation.

14. The method according to claim 1, wherein during the optical system providing step, the visual target and the optical device are placed along an optical axis of the image acquisition module.

15. The method according to claim 1, wherein the image acquisition module is configured to focus on infinite, and a position of the optical device along an axis from the visual target to the image acquisition module is modified.

16. The method according to claim 15,
wherein when an optical power of the optical lens of the optical device is negative, the method further comprises providing an additional optical lens having a positive optical power greater in absolute value than an estimated negative optical power of the optical lens of the optical device, and
wherein the additional optical lens is maintained as close as possible to the optical lens of the optical device during the steps of the method.

17. The method according to claim 1, wherein:
the method further comprises prior to the optical system providing step a focus setting step during which the focus of the image acquisition module is set so as to provide a sharp image of the visual target when placed at an initial distance and acquired directly by the image acquisition module;
a relative position of the visual target along the axis from the visual target to the image acquisition module is modified.

18. The method according to claim 1, further comprising:
a configuration data measuring step during which configuration data indicative of the configuration of the optical system are determined manually or automatically.

19. The method according to claim 1, wherein the acquisition module further comprises a communication module arranged to communicate configuration data indicative of the configuration of the optical system and image data indicative of an image of the visual target acquired by the image acquisition module through the optical device.

* * * * *